(12) United States Patent
Chesnin (10) Patent No.: US 8,328,790 B2
(45) Date of Patent: Dec. 11, 2012

(54) CATHETER TUNNELER

(75) Inventor: Kenneth Chesnin, Philadelphia, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 11/809,163

(22) Filed: May 31, 2007

(65) Prior Publication Data

US 2007/0282274 A1 Dec. 6, 2007

Related U.S. Application Data

(60) Provisional application No. 60/810,612, filed on Jun. 2, 2006.

(51) Int. Cl.
*A61M 25/00* (2006.01)

(52) U.S. Cl. ...................................................... 604/523

(58) Field of Classification Search .................. 604/175, 604/523, 288.01–288.04
See application file for complete search history.

(56) References Cited

U.S. PATENT DOCUMENTS

| | | | |
|---|---|---|---|
| 4,431,426 A | | 2/1984 | Groshong et al. |
| 4,453,928 A | | 6/1984 | Steiger |
| 4,748,808 A | | 6/1988 | Hill |
| 4,832,687 A | | 5/1989 | Smith, III |
| 5,190,529 A | | 3/1993 | McCrory et al. |
| 5,360,407 A | * | 11/1994 | Leonard et al. ............... 604/175 |
| 5,431,661 A | | 7/1995 | Koch |
| 5,637,102 A | | 6/1997 | Tolkoff et al. |
| 5,848,989 A | | 12/1998 | Villani |
| 5,944,732 A | | 8/1999 | Raulerson et al. |
| 6,453,185 B1 | | 9/2002 | O'Keefe |
| 6,565,594 B1 | | 5/2003 | Herweck et al. |
| 6,842,198 B2 | | 1/2005 | Suzuki et al. |
| 6,921,396 B1 | | 7/2005 | Wilson et al. |
| 7,128,734 B1 | | 10/2006 | Wilson et al. |
| 2004/0172003 A1 | | 9/2004 | Wilson et al. |
| 2004/0176739 A1 | * | 9/2004 | Stephens et al. ............... 604/523 |
| 2004/0193119 A1 | | 9/2004 | Canaud et al. |
| 2004/0230204 A1 | | 11/2004 | Wortley et al. |
| 2005/0027282 A1 | * | 2/2005 | Schweikert et al. .......... 604/523 |
| 2006/0015130 A1 | | 1/2006 | Voorhees et al. |
| 2006/0095062 A1 | | 5/2006 | Stephens |

OTHER PUBLICATIONS

Drawing No. 5081, "Split-Cath Tunneler with Tri Ball Tip", Medical Components, Inc. (1997).
International Search Report dated Sep. 10, 2008, PCT/US07/12777 (5 pages).
Written Opinion dated Sep. 10, 2008, PCT/US07/12777 (5 pages).

* cited by examiner

*Primary Examiner* — Victoria P Shumate
(74) *Attorney, Agent, or Firm* — Glenn M. Massina; Fox Rothschild LLP

(57) ABSTRACT

A tunneler (100,800) having a shaft (102,802) with an advancement end (106) and a connection end portion (104, 804) having a lumen insertion tip (108,806) that may define a locating pin. At least one lumen-gripping section (120,818) is defined on the connection end portion spaced from the lumen insertion tip (108,806), and may be a barb section having at least one discrete barb (120), or an array of barbs (124), each with a sharp lumen-biting edge and a tapered lead-in surface (128) extending from the sharp edge toward the locating pin. Also, the lumen-gripping section (818) may be an annulus having a rounded lumen-engaging surface, or may be a circumferential array of nubs having rounded lumen-engaging surfaces. The connection end portion may have a plurality of axially spaced lumen-gripping sections (220,230;818) that may have the same diameters or different maximum dimensions for use with a range of sizes of catheter lumens.

30 Claims, 8 Drawing Sheets

CATHETER TUNNELER

CROSS-REFERENCE TO RELATED APPLICATIONS

This application claims priority from Provisional Patent Application Ser. No. 60/810,612 filed Jun. 2, 2006.

FIELD OF THE INVENTION

This relates to the field of medical devices and more particularly to tunnelers used with catheters for subcutaneous anchoring of a proximal catheter portion during implantation of the catheter into a patient's vasculature.

BACKGROUND OF THE INVENTION

When a catheter assembly is implanted into the vasculature of a patient, the catheter's distal portion is inserted through an incision into the vasculature until the distal tip is precisely located at the desired site, while the proximal portion remains outside the vasculature. The proximal end portion remains external of the patient for access to the catheter for infusion of fluids or withdrawal thereof, or for connections with a hemodialysis apparatus. In order to assure that stress and strain on the catheter assembly does not result in movement of the distal tip from its proper location, especially with a long-term catheter, a lengthy portion of the proximal catheter portion is subcutaneously anchored in the patient by use of a tunneler or a trocar, commonly involving a tunnel route over or near the clavicle as the tunneler pulls the catheter after attachment to an end thereof. Tunneling may be performed either by attachment of the tunneler to the distal catheter end prior to its insertion into the vasculature, or by attachment to the proximal end of the catheter for tunneling after the distal portion has been placed in the vein, termed retrograde tunneling.

Commonly, the tunneler is a generally inflexible cylindrical shaft with a blunt tip for advancing subcutaneously between a location near the catheter's venous entranced site to a tunnel exit site, creating the tunnel. The opposite or connection end of the tunneler is first attachable to the catheter end, and it is later removable from the catheter end after tunneling. There are several known manners of catheter/tunneler attachment, including those disclosed in U.S. Pat. Nos. 4,453,928; 4,832,687; 5,190,529; 5,944,732; 6,453,185; and 6,872,198; and also in U.S. Patent Publications Nos. US 2004/0176739; US 2004/0193119; and US 2005/0027282. Other connections of devices to ends of catheters are disclosed in U.S. Pat. Nos. 5,360,407 and 5,637,102 wherein a proximal end of a catheter is inserted over a barbed locking device, with assistance from an outer locking sleeve to assure the connection.

In U.S. Publication No. US 2005/0027282, an adapter is disclosed attachable to the connection end of the tunneler, wherein an open end of the adapter permits insertion of the catheter end, such as the distal end portion, whereafter a plurality of gripping sections is moved into a gripping relationship to the outside surfaces of the catheter and locked into position; after tunneling the gripping sections are unlocked releasing the catheter for withdrawal.

It is desired to provide a tunneler that is easily used with small-diameter catheters.

It is further desired to provide a tunneler that is easily used with a range of catheter lumen diameters.

It is further desired to provide a tunneler for use with different types of catheters that have either a circular lumen or a D-shaped lumen.

It is further desired to provide a tunneler for small-diameter catheters that produces a subcutaneous track that is close in diameter to the small-diameter catheters.

BRIEF SUMMARY OF THE INVENTION

The tunneler of the present invention is easily attached to a catheter lumen for tunneling, and also may be used with a range of sizes of catheter lumen diameters, particularly lumens of small diameter. Generally, the tunneler of the present invention is a preferably solid shaft of small diameter with a blunt advancement tip and a connection end portion that is so shaped to have one or more lumen-gripping sections. The connection end portion extends to a rounded tip that is insertable into the catheter lumen, and the lumen-gripping sections are spaced axially a small distance from the tip and expand the catheter lumen wall from the inside thereof as the tunneler is urged farther into the catheter lumen end portion, in order to establish a firm grip of the tunneler with the catheter. The insertion tip of the tunneler may have a length of a cylindrical shape for a selected distance, or the tunneler may include a frustoconical section extending from the rounded tip. The insertion tip with a length of a cylindrical shape extending therefrom provides advantages in that the tip is easier to insert into the catheter lumen end, and after insertion has begun, this tip provides stabilization in that the practitioner now will have a convenient way to manually hold the catheter lumen end portion with the insertion tip therewithin thus simplifying the connection procedure.

The or each lumen-gripping section may be a rounded annulus, or a nubbed annulus with several circumferentially spaced nubs with rounded lumen-engaging surfaces; or the or each lumen-gripping section may be an annular frustoconical section concluding in an annular barb or in an array of circumferentially spaced barbs.

In several variations of a first distinct embodiment, the or each lumen-gripping section is a barb section. Each barb section of the connection end portion has a plurality of, such as three or four, barbs preferably equiangularly spaced around the circumference and each thereof having a tapered slope extending toward the connection end of the tunneler that serves as a lead-in surface to facilitate passing of the catheter lumen over the barb while stretching the lumen temporarily. Further, there may be one, two (or more) axially spaced arrays of such barbs where the barbs are axially aligned or are angularly offset from array to array. Between the barbs of each array, the surfaces may be flat or may even be fluted, that is, comprising a shallow axially extending channel. The catheter lumen will be urged onto the connection end of the tunneler and will be retained thereon by the sharp edges of the barbs acting on the internal surfaces of the catheter lumen's wall. The end of the connection end portion is preferably extended to serve as a locating pin that is preferably cylindrical extending a selected length from the tapered lead-in surfaces of the barb section, to a rounded lumen insertion tip, facilitating initial placement of the catheter lumen thereonto and also enabling the practitioner to easily grip the catheter lumen end portion while urging the lumen onto the connection end portion of the tunneler.

In a distinct embodiment, the connection end portion, proximate to the locating pin, may be semi-cylindrical or D-shaped in cross-section such that the barb section is semi-cylindrical, or a pair of such barb sections are each semi-cylindrical, on the opposite side from a common flat surface, with tapered slopes extending toward the connection end; the barb sections may have a single discrete barb or an array of discrete barbs, of different maximum diameters with the smaller one nearer the lumen insertion tip, for use with any of several different sizes of catheter lumens. This embodiment is suitable for insertion into a catheter lumen having a semi-cylindrical or D-shaped cross-section.

In another distinct embodiment, a D-shaped barb section is disposed proximate to the connection end and a round barb section is axially spaced therefrom more distant from the connection end, each having tapered lead-in surfaces extending to the sharp barb edges at the maximum outer dimension of the barb section to facilitate passage of the catheter lumen thereover. Two such D-shaped barb sections, axially staggered from each other, may be disposed adjacent the connection end, and two cylindrical barbs may be axially spaced therefrom more distant from the locating pin of the connection end. This embodiment could be utilized for either a catheter lumen having a D-shaped cross-section or a catheter lumen that is circular in cross-section.

The tunneler of the present invention may be used in a standard tunneling procedure, wherein the tunneler is secured to the distal end of the catheter lumen, whereafter the tunneler is then removed from the lumen; the distal tip portion also may be severed from the catheter to remove the tunneler from the catheter, if desired, prior to inserting an undamaged distal end of the catheter into the vasculature. The tunneler of the present invention may also be used in a retrograde tunneling procedure where the tunneler is attached to the proximal end of the catheter, where, after tunneling, the catheter's proximal end is severed from the catheter to remove the tunneler from the catheter.

However, in a distinctly different set of embodiments, the tunneler may be so configured as to cause minimal or even no damage to the catheter lumen even when the tunneler is forceably removed after tunneling. With these embodiments, the or each lumen-gripping section is a rounded annulus, or a nubbed annulus with several circumferentially spaced nubs with rounded lumen-engaging surfaces, and having no barbs or sharp edges that engage the lumen inside surface. The rounded annulus or the nubbed annulus will expand against the inside surface of the lumen wall to establish a firm friction grip therewith but will not bite into or scrape the lumen wall's inside surface. With these embodiments, damage to the catheter lumen end portion does not occur, and it would be unnecessary to sever the catheter lumen end portion but simply withdraw the tunneler therefrom.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

FIGS. 1 to 4 illustrate a first embodiment of tunneler 100 of a first type, having a cylindrical shaft 102 of a generally constant small diameter extending to a connection end portion 104 and to an advancement tip 106 at an advancement end. Shaft 102 may have, for example, a diameter of from about 0.050 in (1.27 mm) to about 0.118 in (3.00 mm). Connection end portion 104 extends to a locating pin 108 from an abutment shoulder 110. Advancement tip 106 may be rounded or blunt or be sharp, as desired. The tip of locating pin 108 is preferably either rounded or blunt. The connection tip may have a selected length of cylindrical shaft extended to a rounded tip at the end, serving as a locating pin for initial placement of the catheter lumen thereover. For example, locating pin 108 may be from about 0.050 in (1.27 mm) to about 0.125 in (3.18 mm) in length. The locating pin 108 also serves to facilitate manually gripping the catheter end for leverage by supporting the lumen end from collapsing when gripped. Within the connection end portion 104 is a first barb section 120 spaced from abutment shoulder 110 by a smaller diameter shaft portion 122.

First barb section 120 includes a radial array of discrete barbs 124 (seen in FIGS. 2 to 4 and shown as four in number in this embodiment) spaced angularly from each other by indented surfaces 126 which in this embodiment are axially oriented shallow channels or flutes. The indented or recessed surfaces 126 by their design do not press against the lumen interior surface thus reducing drag and permitting the barb section's maximum diameter to be actually larger than the lumen's inside diameter and resulting in increased gripping power. Connection end portion 104 may be defined by machining the connection end of an integral tunneler shaft, or may be molded in an integral one-piece tunneler from biocompatible plastic material, or be molded onto or assembled onto an end of a tunneler shaft component. The tunneler shaft may, if desired, be made from malleable material for shaping the tunneler.

Still referring to FIGS. 1 to 4, extending from locating pin 108 to the discrete barbs 124 of first barb section 120 is a gradually tapered lead-in surface 128, at an angle from axial of from about 15° to about 20°. Lead-in surface 128 facilitates urging the catheter lumen (not shown) onto the connection end portion 104 by gradually stretching wider the catheter lumen end, made easier by the relatively recessed interbarb surfaces 126, until the catheter lumen end passes over the sharp edges of the discrete barb array (the maximum outer dimension or diameter of the barb section) and then the smaller diameter shaft section 122 and abuts the abutment shoulder 110. First barb section 120 with its array of discrete barbs 124 now engage and bite into the internal surface of the catheter lumen and essentially prevent any movement of the catheter lumen from the tunneler under any normal forces encountered during handling for the catheter placement and tunneling. The maximum outer dimension or diameter of the barb section 120 may be from about 0.048 in (1.22 mm) to about 0.095 in (2.4 mm) and be used for tunneling catheters having lumen inner diameters of from about 0.022 in (0.56 mm) to about 0.080 in (2.03 mm).

After tunneling is complete, the catheter lumen is preferably severed near the tunneler as damage to the lumen end portion may occur during forced removal of the tunneler. Alternatively, the tunneler can be designed for forced removal without causing damage to the lumen end portion by careful sizing of the barbs and/or removal of the sharp barb surfaces by deburring methods such as electropolishing. Where the proximal catheter end is tunneled in a retrograde procedure, an extension tube with a luer connector (not shown) may now be affixed to the undamaged proximal lumen end, or a hub with several such extension tubes (also not shown), if the catheter is a multilumen catheter where only one lumen need be connected to the tunneler.

A second embodiment of tunneler 200 is shown in FIGS. 5 to 9. Shaft 202 extends from a connection end 204 to an advancement tip 206 and includes a gradually tapered section 207 adjacent to advancement tip 206. Advancement tip 206 may be rounded or blunt or have a cutting edge, if desired. Tunneler 200 is similar to tunneler 100 and has a first barb section 220 with discrete barbs 224, but in addition has a second barb section 230 spaced a distance therefrom farther from locating pin 208. Second barb section 230 also has an array of discrete barbs 234 (FIGS. 6 to 8 and again shown as four in number) that are shown in axial alignment with the discrete barbs 224 of the first barb section 220. As in tunneler 100, between the discrete barbs 224,234 are indented surface portions 226,236 that are fluted. A smaller diameter shaft section extends from second barb section 230 to abutment shoulder 210, while tapered lead-in surfaces 228,238 extend toward the discrete barb arrays 220,230 from the connection tip 208 and the first barb section, respectively. The second array of barbs 234 provides for engagement with different portions of the interior lumen surface than were engaged by the first array of barbs 224 and thus resulting in additional gripping of the catheter lumen by the tunneler.

Figure 1:
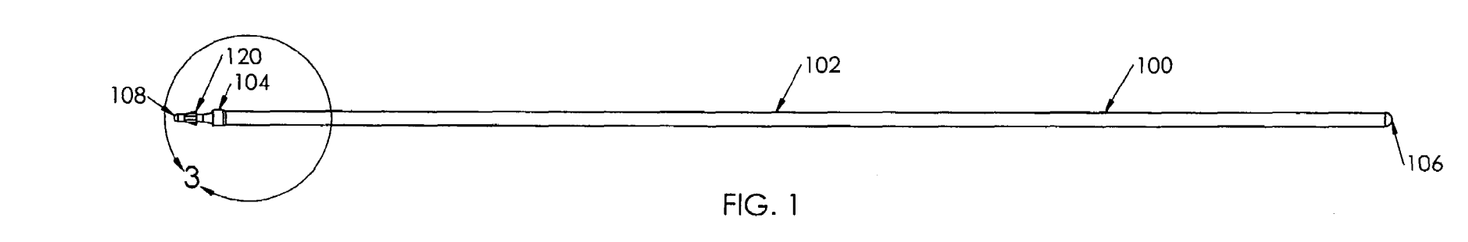
FIG. 1 is an elevation view of a tunneler of a first embodiment of the present invention having a blunt advancement end and a connection end portion having an annular array of barbs.
Figures 2, 3, 4:
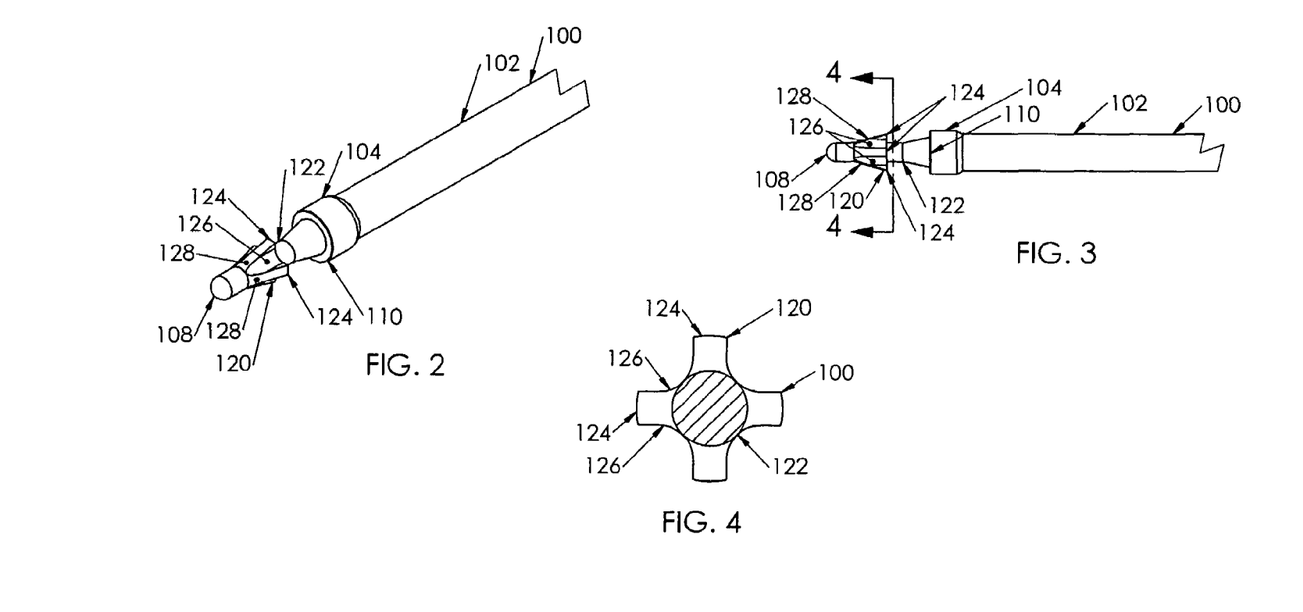
FIGS. 2 and 3 are an enlarged isometric and an enlarged elevation view of the connection end portion of the tunneler of FIG. 1.
FIG. 4 is a cross-sectional view of the tunneler taken along lines 4-4 of FIG. 3.
Figures 5, 6, 7, 8, 9:
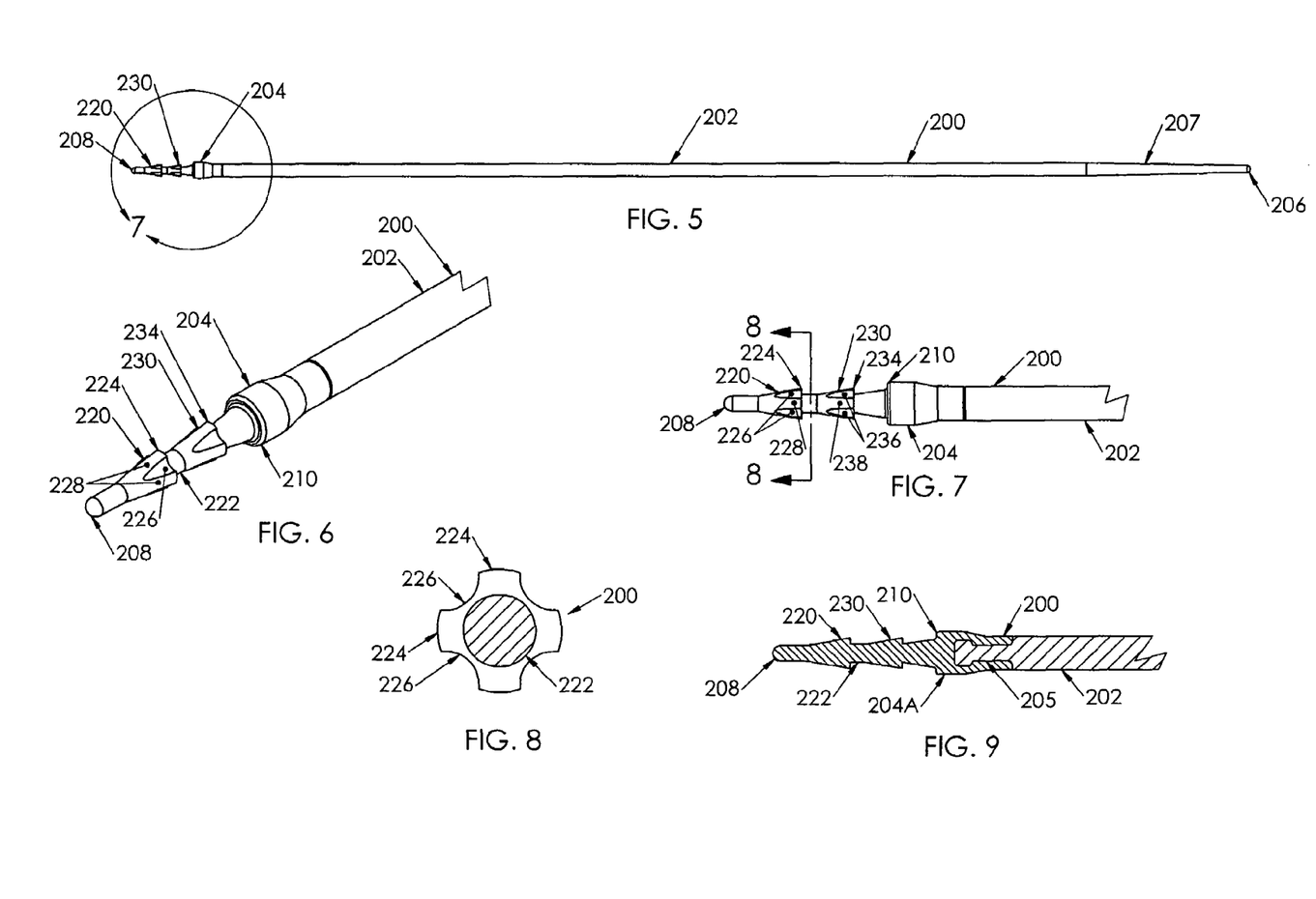
FIGS. 5 to 8 are an elevation and enlarged isometric, elevation and cross-sectional views of a second embodiment of the present invention, similar to FIGS. 1 to 4.
FIG. 9 is a longitudinal cross-section view of the connection end of the tunneler of FIG. 7.

In FIG. 9, a method is shown for manufacturing tunneler 200 by securing a separate connection end portion component 204A to the connection end of the tunneler shaft 202, using a machined boss 205 of an integral shaft and securing the component 204A thereonto. Tunneler 200 may be made of stainless steel; component 204A may be insert molded onto the boss 205 from biocompatible plastic material as is known in the art for medical devices. Other fastening systems may be used to affix separate connection component 204A onto the tunneler shaft, such as by threading or by snap-fit (not shown), for example.

Figures 10, 12, 13, 15:
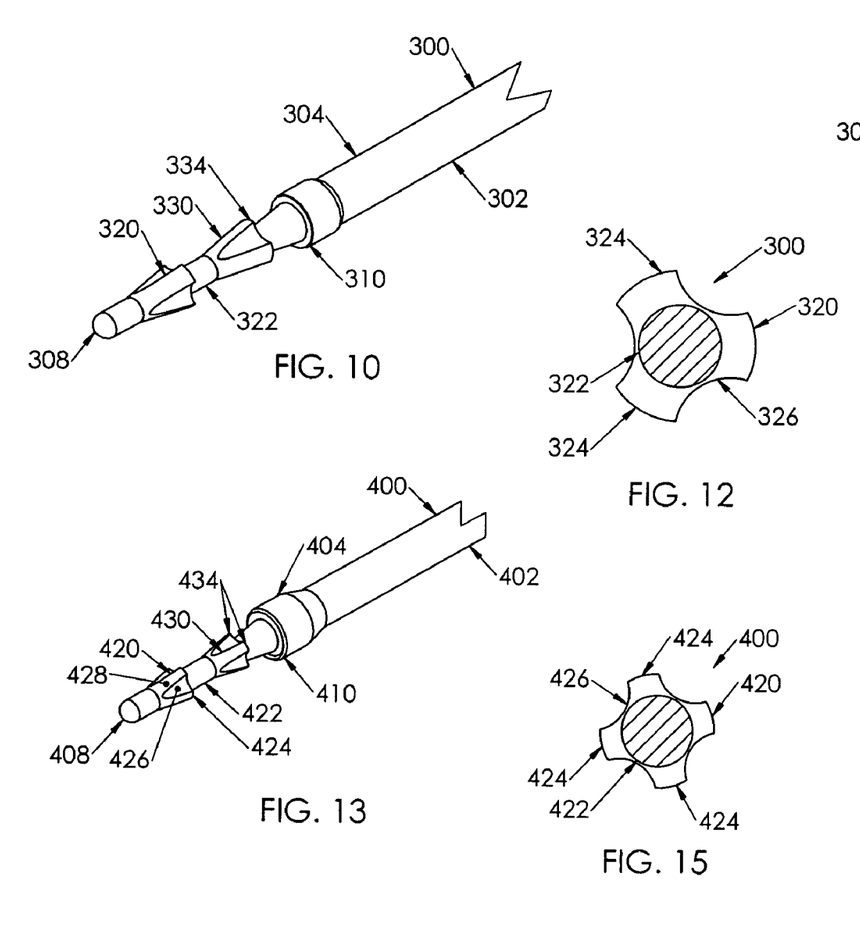
FIGS. 10 to 12 are an isometric, elevation and cross-sectional views of a third embodiment of tunneler similar to FIGS. 6 to 8.
FIGS. 13 to 15 illustrate a fourth embodiment of tunneler.
Figure 11:
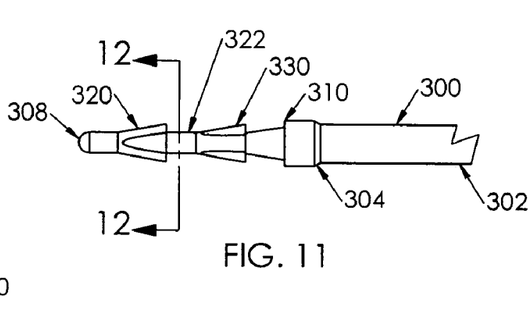

FIGS. 10 to 12 illustrate a third embodiment of tunneler 300. Connection end portion 304 is shown to have a first barb section 320 with three discrete barbs 324 that are equiangularly located, with fluted interbarb surfaces 326 therebetween. A second barb section 330 also has three discrete barbs 334 therearound, wherein the discrete barbs 334 are angularly offset from the angular location of the discrete barbs 324 of first barb section 320. First and second barb sections 320, 330 may have the same maximum diameter at the ends of the respective arrays of discrete barbs, or the respective diameter may be varied, if desired.

Figure 14:
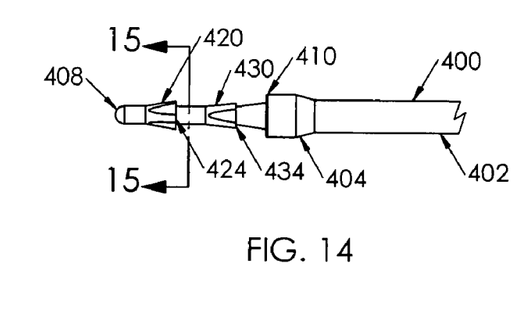

Referring now to FIGS. 13 to 15, tunneler 400 includes a first barb section 420 with four discrete barbs 424 spaced equiangularly therearound, and a second barb section 430 with a similar array of discrete barbs 434 spaced equiangularly thereround. As with tunneler 300, the discrete barbs 434 are offset angularly with respect to discrete barbs 424.

Figures 16, 17, 18, 19, 20:
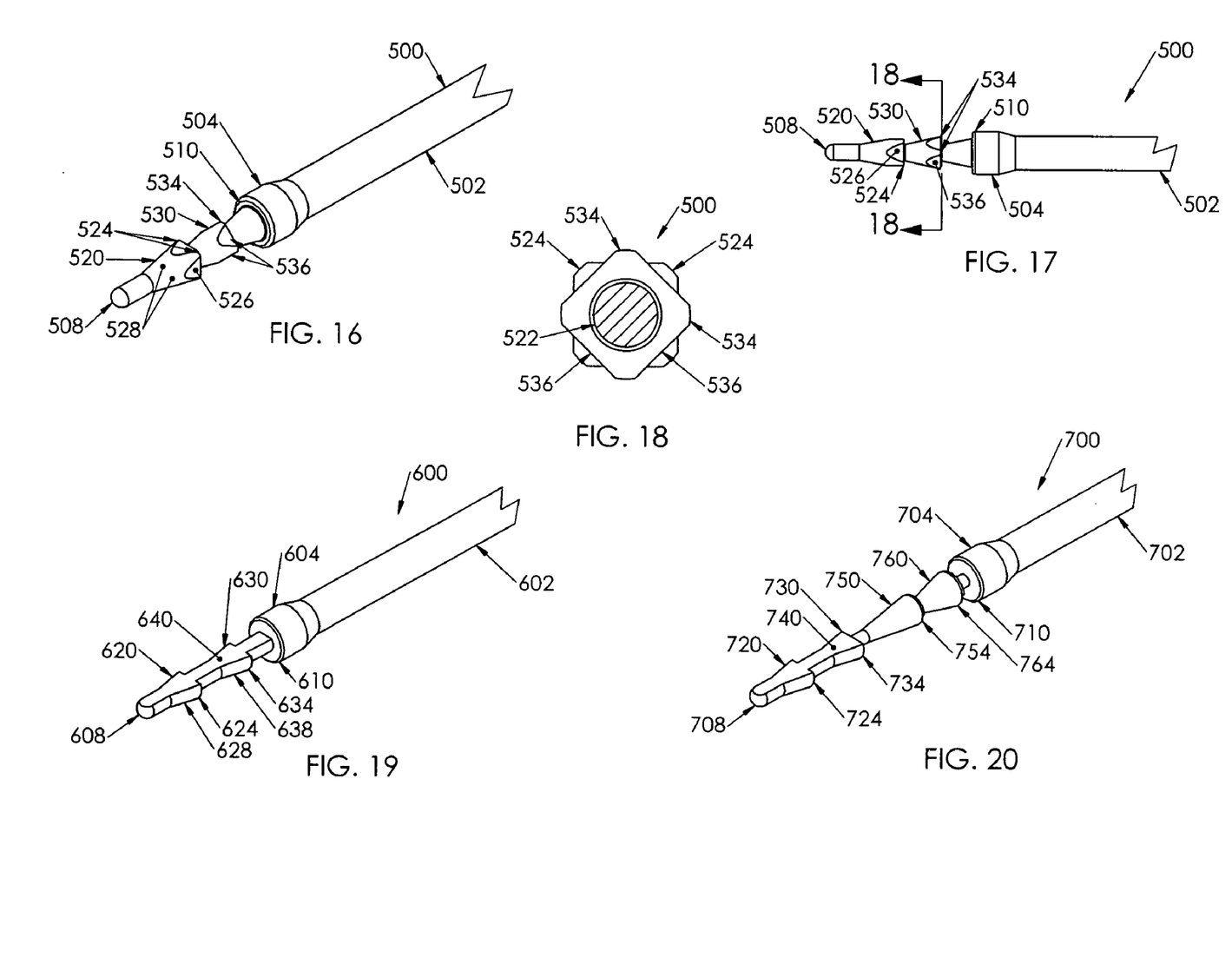
FIGS. 16 to 18 illustrate a fifth embodiment of tunneler.
FIGS. 19 and 20 are isometric views that illustrate sixth and seventh embodiments of tunneler having D-shaped, or D-shaped and circular, cross-sections, respectively.

A fifth embodiment of tunneler 500 is shown in FIGS. 16 to 18, having a first barb section 520 with four discrete barbs 524, and a second barb section 530 having four discrete barbs 534, similar to the embodiment in FIGS. 13 to 15 (although two barbs or more may be used). Lead-in surfaces 528 are tapered; however, the interbarb spaces 526,536 are shown to be flat and not fluted. In this embodiment the discrete barbs 524 may be sharply radiused, with a cross-sectional radius of, for example, about 0.006 in (0.152 mm) at their sharp edges, while the cross-sectional dimension between opposite side flat surfaces may be from about 0.040 in (1.02 mm) to about 0.050 in (1.27 mm). In FIG. 18 it can be seen that the arrays of discrete barbs 534 and 524 are angularly offset. Locating pin 508 is shown as extended in length, facilitating more assured finger-gripping of the lumen during its assembly onto the tunneler's connection end portion.

Tunneler 600 of FIG. 19 is distinct from the embodiments discussed heretofore. Tunneler 600 includes a locating pin 608, a first barb section 620 and a second barb section 630 and an abutment shoulder 610, defining the connection end portion 604. However, connection end portion 604 has a semi-cylindrical, or D-shaped, cross-section, having a flat surface 640, and is adapted for use with the type of catheter lumen having a semi-cylindrical internal cross-section. First and second barb sections 620,630 have each a single discrete barb 624,634, respectively, each also semi-cylindrical in shape and having tapered lead-in surfaces 628,638. Second discrete barb 634 may have an outer dimension greater than that of first discrete barb 624; as a result, tunneler 600 may be used with a range of sizes of catheter lumens of semi-cylindrical interior cross-section, with the larger sizes being urged past the second barb section 630 while those smaller being urged past just the first barb section 620; in each case the catheter lumen would be urged as far onto the connection end portion of the tunneler as possible. Both of the first and second discrete barbs could be arrays of two or more discrete barbs with interbarb surfaces that may be flat or fluted for ease of insertion into a catheter lumen, similar to the embodiments of FIGS. 1 to 18.

In FIG. 20, tunneler 700 has a locating pin 708, first and second barb sections 720,730 having a common flat surface 740 creating a semi-cylindrical cross-section for singular discrete barb sections 724,734 and having tapered lead-in surfaces similar to surfaces 628,638 of FIG. 19. Tunneler 700 additionally has at least a third barb section 750 having a single discrete barb 754 that is annular in cross-section. Tunneler 700 is also seen to have a fourth barb section 760 with an annular discrete barb 764 that may be slightly larger in outer dimension than is third discrete barb 754. All of first, second, third and fourth discrete barbs could be arrays of two or more discrete barbs with interbarb surfaces that may be flat or fluted for ease of insertion into a catheter lumen, similar to the embodiments of FIGS. 1 to 18. Thus, tunneler 700 is useful with catheter lumens that are either semi-cylindrical or circular in cross-section and are of a range of sizes and being quite universal.

Figure 21:
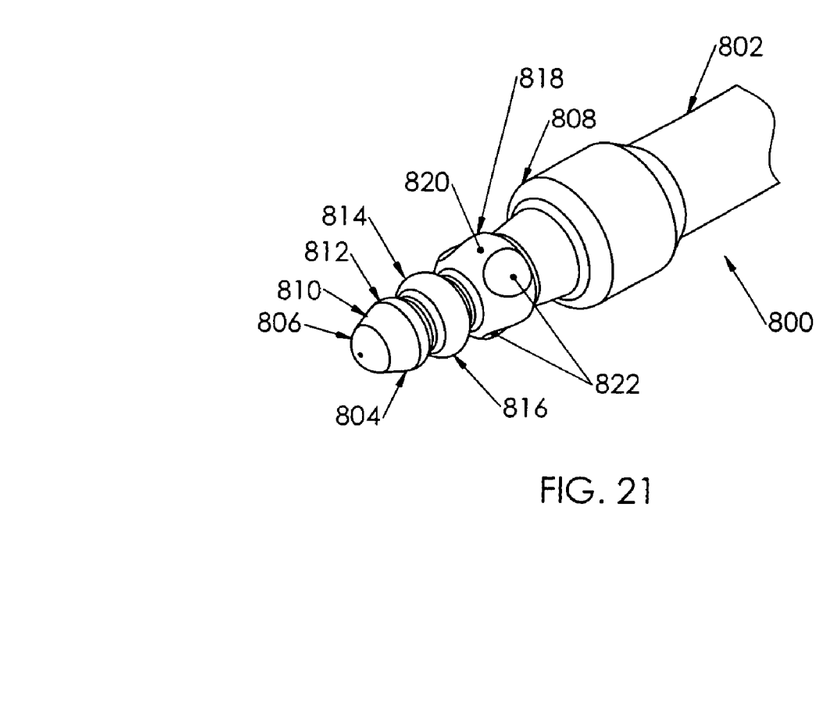
FIGS. 21 to 23 are an isometric view, an elevation view and a cross-section view respectively, of an eighth embodiment of tunneler connection portion, with FIG. 23 taken along lines 23-23 of FIG. 22.
Figure 22:
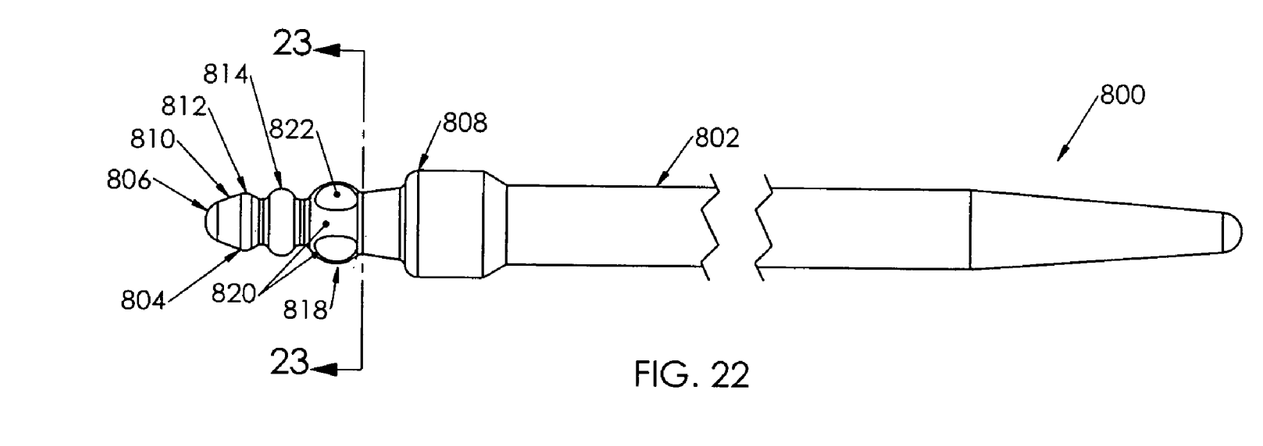
Figure 23:
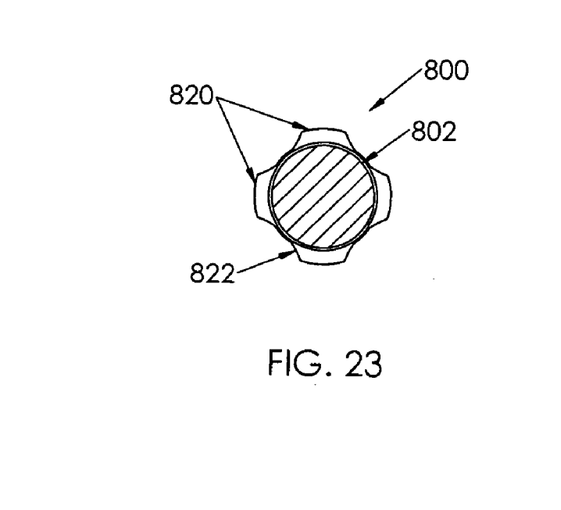

A set of distinctly different embodiments of the tunneler of the present invention is depicted in FIGS. 21 to 32. Tunneler 800 of FIGS. 21 to 23 is seen to have a shaft 802 and a connection end portion 804 concluding in a lumen insertion tip 806 that is rounded, and an abutment shoulder 808. Adjacent to rounded tip 806 is a frustoconical enlargement 810 to initiate expansion of the lumen diameter during insertion of the connection end portion into the catheter end, with enlargement portion having a rounded rearward surface 812 (i.e., no sharp barb edge). Spaced rearwardly from enlargement 810 is a rounded annulus 814 with a rounded lumen-engaging surface 816, annulus 814 preferably being larger in diameter than enlargement 812, and, again, having no sharp barb edge. Also, preferably, an additional lumen-gripping section 818 is spaced rearwardly from annulus 814 and has an even larger diameter as defined by the rounded surfaces of lumen-engaging nubs 820 that are spaced preferably equidistantly about the circumference of lumen-gripping section 818, with the nubs 820 separated from each other by indentations 822 that may be akin to flutes 126 or flats 526 of tunnelers 100 and 500 of FIGS. 4 and 16, respectively. With all surfaces engaging the inner wall surface of the catheter lumen end portion being rounded, minimal or no damage occurs to the lumen by insertion thereinto of the tunneler connection end portion or during the tunneling procedure or the subsequent withdrawal therefrom of the tunneler.

Figure 24:
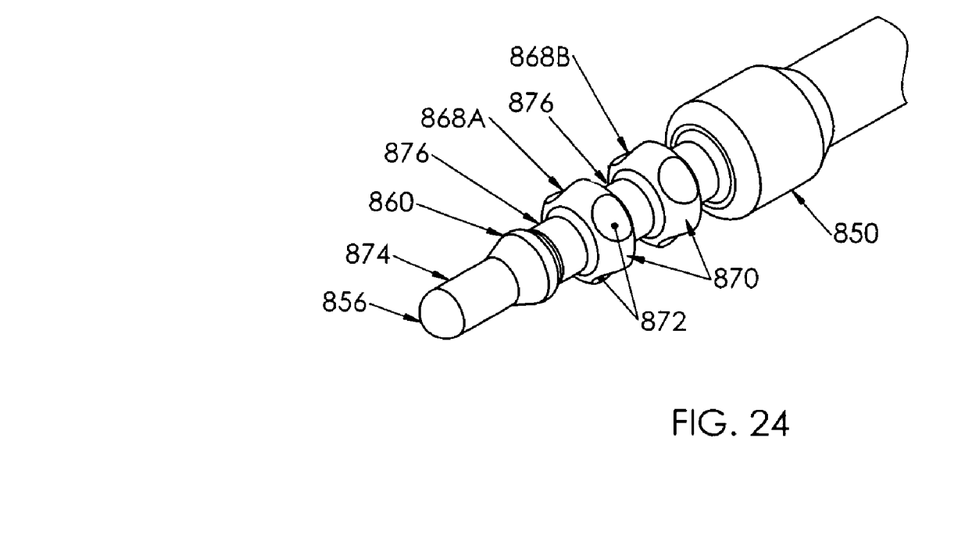
FIGS. 24 to 32 are views similar to those of FIGS. 21 to 23, of three additional embodiments similar to that of FIG. 21.
Figure 25:
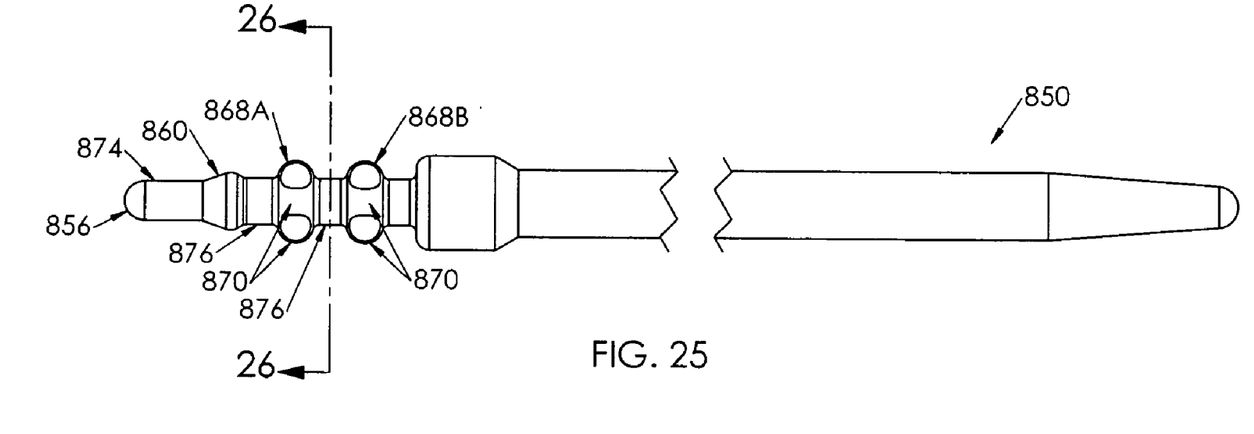
Figure 26:
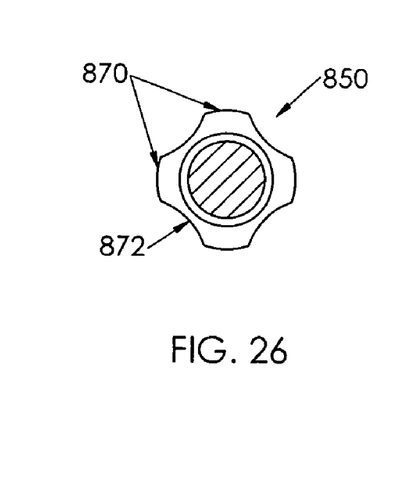

In FIGS. 24 to 26 is shown a tunneler 850 similar in many respects to tunneler 800. A length of cylindrical small diameter section 874 is immediately adjacent to lumen insertion tip 856, similar to sections in the tunnelers of FIGS. 1 to 20, providing the practitioner with the ability to hold the catheter lumen length during initial states of tip insertion thereinto. A frustoconical enlargement 860 is adjacent the cylindrical section 874. Two lumen-gripping sections 868A and 868B are utilized in this embodiment, similar to lumen-gripping section 818 of FIGS. 21 to 23, having four lumen-engaging nubs 870 spaced about the circumference, separated from each other by indentations 872. Lumen-gripping sections 868A, 868B are shown separated by small diameter shaft sections 876, thus defining a longer connection end portion for the tunneler.

Figure 27:
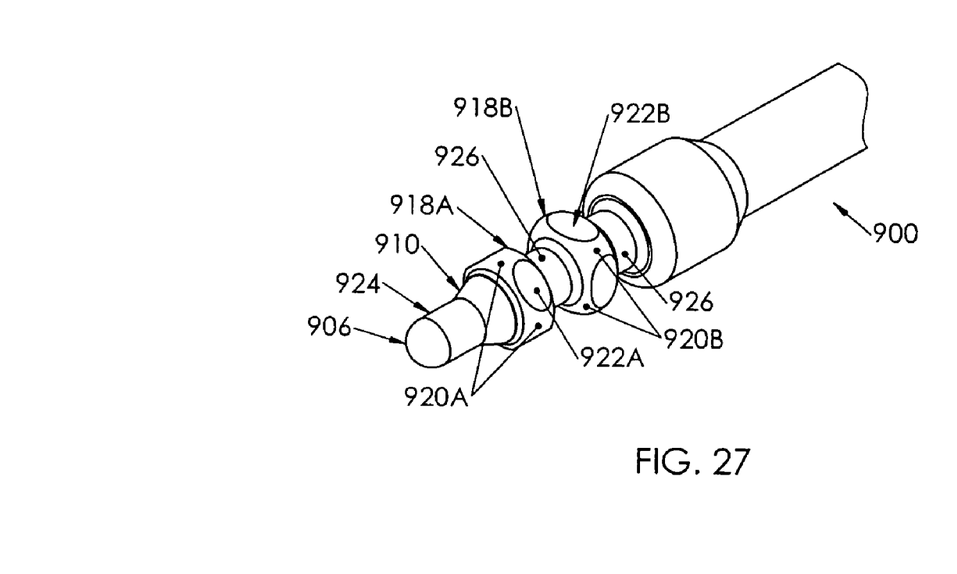
Figure 28:
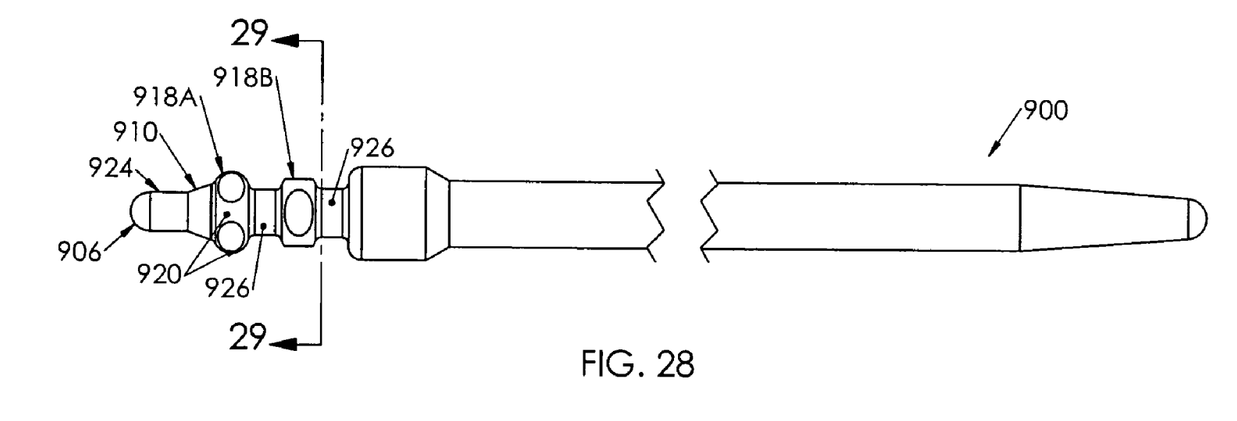
Figure 29:
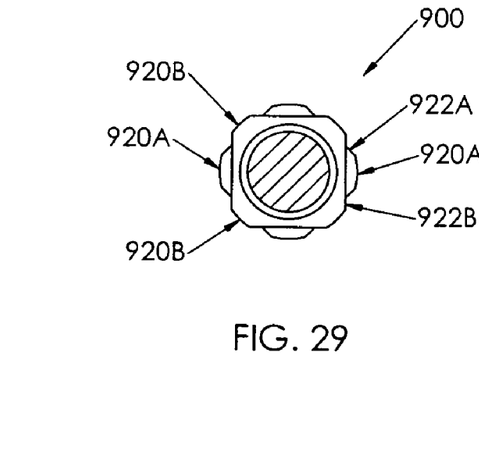

Tunneler 900 of FIGS. 27 to 29 has a cylindrical shaft section 924 of selected length adjacent to lumen insertion tip 906, similar to that of tunneler 100 of FIGS. 1 to 4, enabling the practitioner to be able to grasp the catheter lumen end portion during insertion of the lumen insertion tip of the tunneler facilitating connection of the tunneler to the catheter end. Adjacent to cylindrical section 924 is frustoconical section 910. Immediately adjacent to frustoconical section 910 is first lumen-gripping section 918A having an array of nubs 920A. Tunneler 900 has a second gripping section 918B that is spaced rearwardly from first lumen-gripping section 908A but is rotated 45 degrees therefrom so that its lumen-engaging surfaces 920B and indentations 922B are angularly offset to engage the interior lumen wall at locations untouched by the lumen-engaging surfaces 920A and indentations 922A. It may also be seen that nubs 920B may have different shapes and dimensions from nubs 920A.

Figure 30:
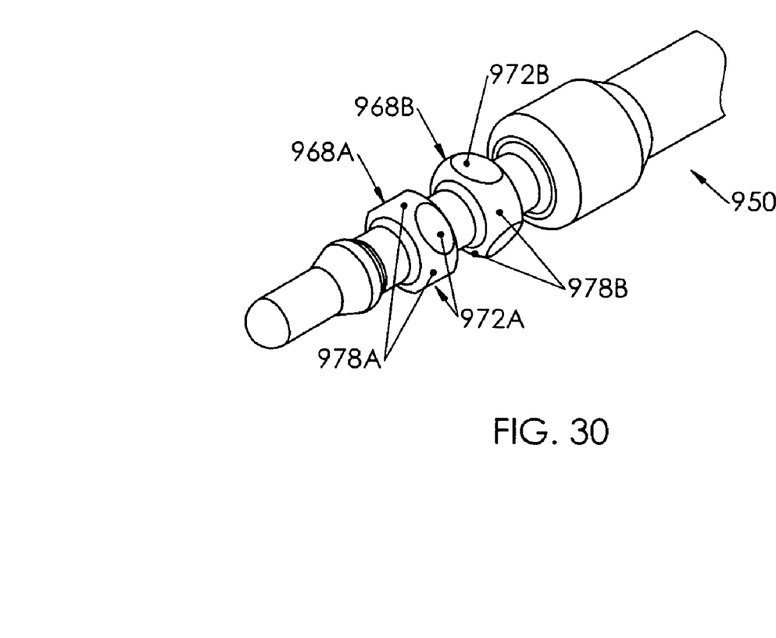
Figure 31:
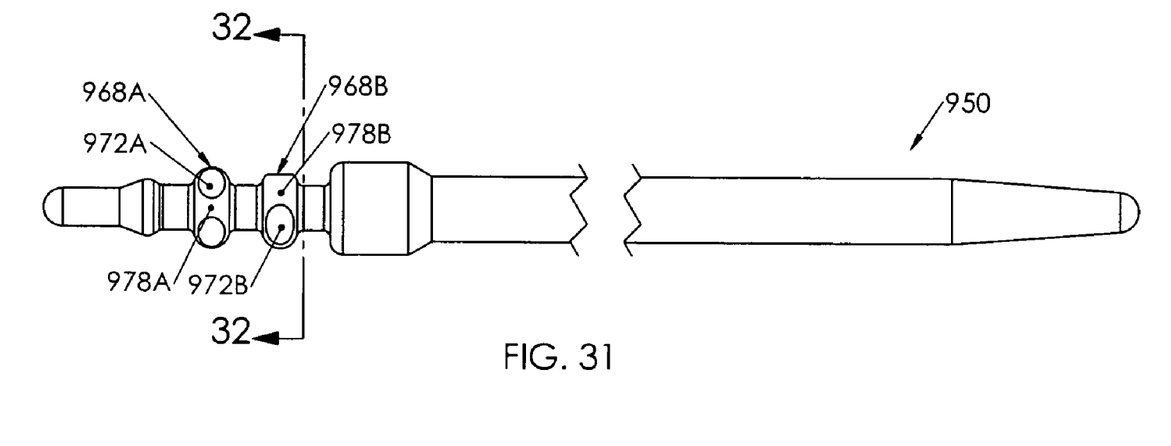
Figure 32:
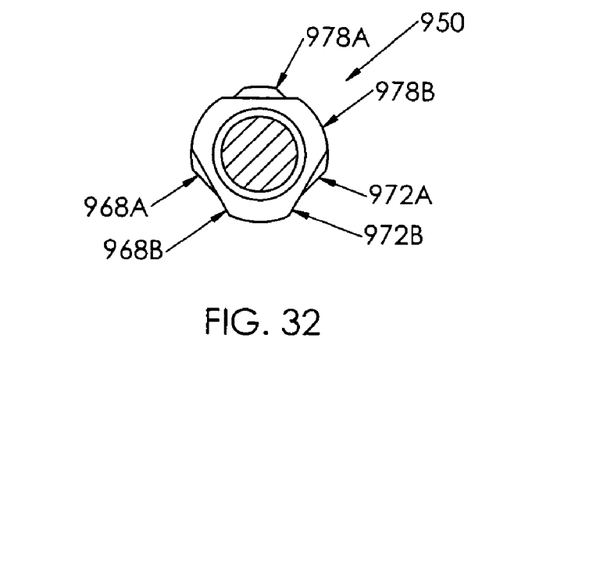

In FIGS. 30 to 32 is seen tunneler 950, which is similar to tunneler 900 of FIGS. 27 to 29 except that its first lumen-gripping section 968A, has four nubs 978A while second lumen-gripping section 968B have an array of three nubs 978B; thus, the nubs can vary in number, and may also vary in shape and dimension. The nubs are separated by flat indentations 972 (FIG. 32) and have the angular offset of tunneler 900.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A tunneler for subcutaneous tunneling of a catheter, comprising:
   a shaft having an advancement end and a catheter connection end, the catheter connection end having a catheter connection end portion extending to a lumen insertion tip and having at least one lumen-gripping section about the circumference of the catheter connection end portion near the lumen insertion tip and further having a longitudinal axis,
   wherein each at least one lumen-gripping section defines, at a plane extending radially from and perpendicular to the longitudinal axis of the catheter connection end portion and extending through the respective at least one lumen-gripping section, a continuous circumferential surface including a plurality of lumen-engaging surface portions defined by the circumferential surface circumferentially alternating with a plurality of non-engaging surface portions defined by the circumferential surface, each lumen-engaging surface portion radially spaced from the longitudinal axis more than the non-engaging surface portions circumferentially adjacent thereto.

2. The tunneler of claim 1, wherein the catheter connection end portion concludes in a cylindrical shaft portion of selected length concluding in a lumen insertion tip that is rounded as it intersects a longitudinal axis of the shaft.

3. The tunneler of claim 2, wherein the cylindrical shaft portion is from about 0.050 in, to about 0.125 in, in length.

4. The tunneler of claim 1, wherein the shaft includes a catheter abutment shoulder adjacent the connection end portion.

5. The tunneler of claim 1, wherein the shaft has a diameter of from about 0.050 in, to about 0.118 in.

6. The tunneler of claim 1, wherein the catheter connection end portion is affixed onto the shaft.

7. The tunneler of claim 1, wherein the catheter connection end portion is molded onto a boss of the shaft.

8. The tunneler of claim 1, wherein the shaft, the advancement end and the catheter connection end define an integral, one-piece member that is solid from end to end.

9. The tunneler of claim 8, wherein the integral member is metal and the configuration of the catheter connection end portion is defined by machining.

10. The tunneler of claim 1, wherein each lumen-engaging surface portion is a lumen-engaging barb section, and each barb section includes a tapered lead-in surface extending from a barb edge toward the lumen insertion tip.

11. The tunneler of claim 10, wherein the connection end portion includes more than one lumen-gripping section spaced axially therealong.

12. The tunneler of claim 11, wherein the connection end portion includes two lumen-gripping sections spaced axially therealong.

13. The tunneler of claim 12, wherein the outer perimeter of one of the lumen-gripping sections is larger than the outer perimeter of the other lumen-gripping section.

14. The tunneler of claim 12, wherein the lumen-engaging surface portions of the first and second lumen-gripping sections are angularly offset.

15. The tunneler of claim 11, wherein one of the lumen-gripping sections is defined by a first barb section of semi-cylindrical D cross-section and another of the other lumen-gripping sections is defined by a second barb section of semi-cylindrical D cross-section, wherein for each barb section the flat portion of the D cross-section defines one of the non-engaging surface portions and a flat or flute along the arcuate portion defines one of the non-engaging surface portions.

16. The tunneler of claim 15, wherein the first barb section of semi-cylindrical cross-section is closer to the lumen insertion tip and has a selected maximum outer dimension and the second barb section a greater selected maximum outer dimension.

17. The tunneler of claim 15, further including at least one additional barb section that is annular in cross-section and is disposed farther from the lumen insertion tip than the first and second barb sections.

18. The tunneler of claim 17, wherein the at least one additional barb section defines a continuous, non-compressible circumferential surface including a plurality of lumen-engaging barbs extending along an outer perimeter defined by the circumferential surface and alternating with non-engaging surface portions between the barbs.

19. The tunneler of claim 18, wherein the barbs are equi-angularly spaced around the catheter connection end portion.

20. The tunneler of claim 1, wherein the lumen-gripping section includes three lumen-engaging surface portions separated by three non-engaging surface portions.

21. The tunneler of claim 1, wherein the lumen-gripping section includes four lumen-engaging surface portions separated by three non-engaging surface portions.

22. The tunneler of claim 1, wherein the non-engaging surface portions are flat.

23. The tunneler of claim 1, wherein the non-engaging surface portions are fluted.

24. The tunneler of claim 1, wherein the at least one lumen-gripping section has at least one rounded lumen-engaging surface portion defined as a nub.

25. The tunneler of claim 24, wherein at least one lumen-gripping section has a circumferential array of nubs defined at each lumen-engaging surface portion.

26. The tunneler of claim 25, wherein the tunneler connection end portion has more than one lumen-gripping section with the lumen-engaging surface portions thereof defined as rounded nubs.

27. The tunneler of claim 26, wherein each at least one lumen-gripping sections has its nubs angularly offset from the nubs of another at least one lumen-gripping section.

28. The tunneler of claim 25, comprising three nubs.

29. The tunneler of claim 25, comprising four nubs.

30. A tunneler for subcutaneous tunneling of a catheter, comprising:
   a shaft having an advancement end and a catheter connection end, the catheter connection end having a catheter connection end portion extending to a lumen insertion tip and having at least one lumen-gripping section about the circumference of the catheter connection end portion near the lumen insertion tip,
   wherein each at least one lumen-gripping section defines a continuous, circumferential surface including a plurality of lumen-engaging surface portions extending along a maximum diameter of the surface and circumferentially alternating with a plurality of non-engaging surface portions, each non-engaging surface portion recessed from the maximum diameter.

* * * * *